United States Patent [19]

Thomas et al.

[11] Patent Number: 5,298,486
[45] Date of Patent: Mar. 29, 1994

[54] USE OF PYRIDINES AS PERFUMING AND FLAVORING INGREDIENTS

[75] Inventors: Alan F. Thomas, Borex; Frederico Bassols, Onex, both of Switzerland

[73] Assignee: Firmenich S.A., Geneva, Switzerland

[21] Appl. No.: 731,582

[22] Filed: Jul. 17, 1991

[30] Foreign Application Priority Data

Aug. 10, 1990 [CH] Switzerland .................... 260690

[51] Int. Cl.$^5$ ................................ A61K 7/46
[52] U.S. Cl. ...................... 512/10; 426/537; 252/174.11; 252/86; 424/76.4
[58] Field of Search ............. 512/10; 546/348; 426/537; 252/174.11, 8.6; 424/76.4

[56] References Cited

U.S. PATENT DOCUMENTS

| | | | |
|---|---|---|---|
| 3,381,691 | 5/1968 | Schumacher et al. | 131/17 |
| 3,669,908 | 6/1972 | Hall | 252/522 |
| 3,702,253 | 11/1972 | Winter et al. | 99/71 |
| 3,716,543 | 2/1973 | Hal | 260/290 |
| 3,914,227 | 10/1975 | Pittet et al. | 546/348 |
| 4,005,227 | 1/1977 | Winters et al. | 546/348 |
| 4,374,051 | 2/1983 | Naf et al. | 252/522 |

FOREIGN PATENT DOCUMENTS

| | | | |
|---|---|---|---|
| 548167 | 4/1974 | Switzerland | 512/10 |
| 1156483 | 6/1969 | United Kingdom | 512/10 |
| 2070931 | 6/1981 | United Kingdom | 512/10 |

OTHER PUBLICATIONS

Pevsner et al., J. Biol. Chem., vol. 265, pp. 6118–6125 (1990).
Vusupov et al., Chem. Abst., vol. 105, #190,920g (1986).
Buttery et al., Chem. Abst., vol. 87, #182766f (1977).
Heckman et al., Chem. Abst., vol. 95, #39305q (1981).

*Primary Examiner*—James H. Reamer
*Attorney, Agent, or Firm*—Pennie & Edmonds

[57] ABSTRACT

Pyridines of formula

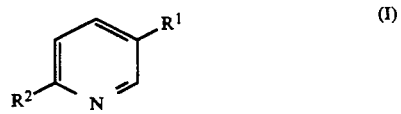

wherein R$^1$ stands for a saturated linear alkyl radical having 6 to 8 carbon atoms, or for a 4-methylhexyl radical, and R$^2$ represents either a hydrogen atom or, when R$^1$ has 6 carbon atoms, a hydrogen atom or a methyl radical, are used in the reconstitution of orange essential oil as well as for flavoring orange juice. They are also useful ingredients in the reproduction of flavors of the seafood, fishy type.

Pyridines (I) are also used in perfumery.

17 Claims, No Drawings

USE OF PYRIDINES AS PERFUMING AND FLAVORING INGREDIENTS

BRIEF SUMMARY OF THE INVENTION

The present invention relates to the perfume and flavor industries. It concerns more particularly a process to confer, improve, enhance or modify the organoleptic properties of a perfuming or flavoring composition, or a perfumed or flavored article, which process comprises adding to said composition or article a compound of formula

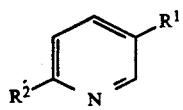

wherein $R^1$ stands for a saturated linear alkyl radical having 6 to 8 carbon atoms, or for a 4-methylhexyl radical, and $R^2$ represents either a hydrogen atom or, when $R^1$ has 6 carbon atoms, a hydrogen atom or a methyl radical.

The invention also provides a perfuming composition or a perfumed article containing as active ingredient a compound of formula (I).

It is another object of the invention to provide a flavoring composition or a flavored article containing as active ingredient a compound of formula (I) as defined in claim 1 essentially in its pure form.

A preferred embodiment of the invention provides a process to confer, improve, enhance or modify the citrus flavor character of a flavoring composition or a flavored article, which process comprises adding to said composition or article a compound of formula (I) as defined in claim 1.

A citrus flavor character flavoring composition or flavored article containing a compound of formula (I) essentially in its pure form, is another object of the invention. The latter further contemplates a process to improve the orange type flavor character in an article such as a foodstuff, a beverage, a chewing gum, a toothpaste or a pharmaceutical preparation, which process comprises adding to said article a compound of formula (I) in a concentration of between about 20 ppb and 5 ppm of the total weight of the article.

BACKGROUND OF THE INVENTION

Organoleptically useful pyridines are known from the prior art. For example, U.S. Pat. Nos. 3,669,908 and 3,716,543 describe pyridines having alkenyl or alkadienyl lateral chains and which possess aromatic notes reminiscent of seafood flavors. It is also disclosed in these references that the said pyridines impart to the compositions in which they are incorporated marine type notes such as "seaside", "seafood", as well as spicy or yet woody-amber notes.

On the other hand, U.S. Pat. No. 3,702,253 discloses alkyl- or alkenyl-substituted pyridines which are typical of coffee flavor and which possess aromatic notes wherein the bitter, green, roasted, astringent and nutty characters are strongly represented.

Other prior art references disclose, for example, alkyl-substituted pyridines which are useful in the flavoring of tobacco [see, for example, U.S. Pat. No. 3,381,691], or yet particularly adapted to the preparation of perfuming compositions, while also useful for the flavor industry [see U.S. Pat. No. 4,374,051.

With the exception of 3-(4-methylhexyl)pyridine which is novel, the chemical structure of the compounds of formula (I) has been known for some time. Yet, we have not found in the prior art any mention of their organoleptic properties. Furthermore, none of above-cited prior art references describe any compounds possessing the surprisingly useful combination of aromatic notes of the compounds according to the present invention.

THE INVENTION

We have now discovered that the compounds of formula (I) described above possess very interesting flavoring properties and that they develop, at high dilutions, aromatic notes which are very useful for flavoring foodstuffs and beverages, as well as other consumer products traditionally flavored.

Compounds (I) develop in fact aromatic notes of the fruity, citrus type, which can be accompanied by marine type flavors. Thus, 3-hexylpyridine, for example, develops a fruity, citrus aroma, reminiscent of the fruit's peel flavor, mandarine in particular. On the other hand, 3-heptylpyridine possesses a less fruity flavor character (which is still reminiscent of the peel of the fruit), fatty, metallic and accompanied by a fishy note. It also possesses a melon type note. As for 8-octylpyridine, its flavor note is fruity, juicy, together with a seafood and seaweed character. Yet another useful compound of formula (I) is 5-hexyl-2-methylpyridine which possesses a fatty, fishy, metallic flavor, together with a mandarine type fruity character. This combination of fruity-citrus notes, with marine type flavors is totally unexpected and surprising for this type of compounds and renders the compounds of the invention particularly useful in both fruity-type, namely citrus, flavor applications and savoury type ones, as described in the examples presented further on.

The present invention results from our fortuitous discovery that the pyridines of formula (I) were components of the orange essential oil. Their presence in this oil, hitherto unsuspected, has now been detected thanks to the use of a sophisticated analysis technique, resorting to gas chromatographic methods. They are therefore natural products whose presence in the essential oil of orange had eluded up to now the numerous analyses to which this oil had been submitted.

The compounds of the invention were extracted from an orange essential oil obtained by cold pressing of Florida oranges. This essential oil (100 kg) was extracted under stirring and $N_2$ with sulfuric acid (10% aqueous; $2 \times 1$ l) and then water ($2 \times 1$ l). The mixture was stirred for 4 min and then decanted for about 2 h between each operation. In order to eliminate the emulsions in the aqueous phase, a Hyflow super cell and Büchner filtration were used before extracting. The combined acid and aqueous phases were washed with pentane ($3 \times 500$ ml, using very pure commercial pentane), then rendered alkaline with solid sodium carbonate. The alkaline solution was extracted with pentane ($3 \times 200$ ml). This organic phase was then dried over $MgSO_4$ and concentrated ($40°/13 \times 10^3$ Pa) to yield about 280 mg of product. The latter was submitted to another extraction by diluting in 20 ml of ethyl acetate and extracting with $H_2SO_4$ ($2 \times \sim 7$ ml) and $H_2O$ ($2 \times \sim 7$ ml). The aqueous phase was rendered alkaline with solid sodium carbonate and extracted with ethyl acetate (3×10 ml). After drying over MgSO₄ and concentrating, about 8 mg of extract were obtained, consisting essentially of nitrogen-containing products. This extract was directly injected in a GC-MS (gas chromatography-mass spectrometry) apparatus.

Some pyridines thus identified, as well as their retention times and mass spectra are presented hereinafter:

| Compound | Retention time/min | |
|---|---|---|
| | Supelcowax 10 column 15 m | SPB-1 column 60 m |
| 1. 3-hexylpyridine | 10.20 | 22.29 |
| 2. 3-heptylpyridine | 11.99 | 25.39 |
| 3. 3-octylpyridine | 15.50 | 28.38 |
| 4. 3-phenylpyridine | 18.15 | 25.10 |
| 5. 5-hexyl-2-methylpyridine | 11.16 | 24.14 |
| 6. 3-(4-methylhexyl)pyridine | 10.39 | 27.59 |
| 7. 2-methyl-5-phenylpyridine | 18.37 | 30.66 |
| 8. 3-(4-methyl-1-phenyl)pyridine | 19.80 | 32.09 |

Mass spectra:
1. 163($M^+$, 10), 162(10), 148(3), 134(9), 120(33), 107(14), 106(85), 93(100), 92(70).
2. 177($M^+$, 4),162(2),148(6),134(13),120(15),107(15),106(75), 93(100), 92(40).
3. 191($M^+$, 11), 162(8),148(14),134(7),120(18),107(19),106(98), 93(100), 92(40).
4. 155($M^+$, 100), 154(53),128(11),127(15),126(7),102(12).
5. 177($M^+$, 10), 176(5),162(2),148(4),134(15),120(38),107(35), 106(100), 93(4), 92(3).
6. 177($M^+$, 10), 176(8),162(9),148(30),134(5),120(30),107(33), 106(71), 93(100), 92(88), 65(26), 57(25), 43(28), 41(24), 39(15).
7. 169($M^+$, 100), 168(20),167(10),154(4),141(23),127(7),115(15), 102(12), 85(7), 77(8),63(9).
8. 169($M^+$, 100), 168(60), 167(18), 154(6), 141(10), 126(4), 115(14), 91(9), 84(7), 71(13),63(7).

The structure of the pyridines of formula (I), inferred from their mass spectra above, was confirmed by synthesis. The methods used in the preparation of these compounds are described further on.

In spite of the many prior art studies carried out on orange oil, which made it possible to identify more than 200 components [see in "Volatile Compounds in Foods-Qualitative and Quantitative Data", Vol I, pages 44–49, ed. TNO, Holland (1989) and references therein], no pyridine had been detected up to now in this essential oil. We have now discovered, amongst others, those above-cited which are present in extremely small amounts, of the order of 1 ppm. Amongst these pyridines, it became apparent that the compounds of formula (I) according to the invention made a determining contribution to the typical orange flavor and that, as a result, they could be used in the reconstitution of the essential oil of this fruit, when used at high dilution.

The compounds of the invention thus provide an original solution to the problem of the reconstitution of the specific orange flavor. In this context, it should be noted that their presence in orange essential oil was totally unexpected and it would have been impossible to predict that these pyridines could develop, at high dilution, aromatic notes that are quite essential for the reproduction of the gustative character of the actual fruit and, in particular, of its juice.

However, the organoleptic properties of these compounds are such that their field of application is far more varied than that defined by the reconstitution of natural orange essential oil alone. They find, in effect, wide application in the flavor industry, where they can be used to confer, improve, enhance or modify typical citrus notes and more particularly that of orange. For example, they impart to orange oil a more juicy and stronger flavor, more typical of the zest of the fruit. In addition, they can also be advantageously used in other citrus type applications, such as lemon, grapefruit, lime, mandarine or tangerine type flavors.

Furthermore, they are also very useful in a totally different flavor domain, that of savory and spicy foodstuffs, wherein they develop or reinforce the fishy or seafood character of the food.

In order to produce the desired flavoring effects, pyridines (I) are preferably used at very low concentrations. Thus, interesting effects have already been obtained with concentrations of the order of 20 ppb of pyridine (I), relative to the total weight of the flavor composition in which this pyridine is incorporated. Such concentrations can go up to 5 ppm for example, depending on the type of application.

The compounds of the invention can be used to flavor various articles such as foodstuffs, beverages, chewing gums, toothpastes or even pharmaceutical preparations. Foodstuffs that may be thus flavored include ice-creams, dessert creams, yogurts, dairy products in general, bakery or confectionery products, syrups, candies, jams or even, soups and stocks, extracts for the preparation of soups and sauces, or, in general, fish or seafood based products, or products that are desired to emulate these latter flavor characters. One can also cite foods such as chips and crackers, snacks or other.

The compounds of formula (I) are incorporated into the foods, beverages, chewing gums, toothpastes or pharmaceutical preparations to be flavored according to the methods current in the art, either alone, or in admixture with other natural or synthetic flavoring ingredients. They can be used as such, or in solution in one of the usual edible solvents such as triacetin, ethanol or propylene glycol, or yet in admixture on a solid carrier, for example, dextrine or gum arabic.

Pyridines (I) are also useful as perfuming ingredients. For example, 3-heptylpyridine, a preferred perfuming ingredient according to the invention, develops an odor note reminiscent of α-sinensal, or 2,6,10-trimethyl-2,6,11-dodecatrien-1-al, having a mandarine character and a fresh connotation. This compound imparts to the compositions to which it is added a natural odor, reminiscent of the orange flower odor.

Another preferred perfuming ingredient according to the invention is 3-hexylpyridine which possesses a fruity, fatty odor, reminiscent of orange.

Pyridines (I) can be advantageously used both in fine and functional perfumery, for the preparation of perfuming compositions and perfumed articles. Amongst the latter, one can cite perfumes and colognes, soaps, bath and shower gels, shampoos and other hair-care products, cosmetic preparations and body or air deodorants. They find also useful application for perfuming detergents, fabric softeners or household products.

When pyridines (I) are used in this type of applications, interesting fragrance effects can be obtained at low concentrations, typically of the order of 0.01 to 0.2% by weight of pyridine, relative to the weight of the composition in which it is incorporated.

The monosubstituted compounds of formula (I), i.e., the 3-alkylpyridines, were prepared according to a general method which is described hereinafter with regard to 3-hexylpyridine. A solution of sodium amide in liquid ammoniac was prepared by adding small pieces of sodium to about 300 ml of liquid ammoniac containing 0.1 g of ferric nitrate, until the total amount of sodium added was 5.78 g. Once the reaction was completed, 20.48 g of 3-methylpyridine were added at −30° C. (10 min) and then 36.24 g (29.8 ml) of pentyl bromide over 15 min. The mixture was further stirred for 15 min and then the ammoniac was allowed to evaporate and iced water was added to complete the hydrolysis. The mixture was extracted with ether (twice) and this extract was washed with water and again extracted with HCl (10% aqueous, 4 times) and once with water. The combined aqueous phases were rendered alkaline with a 20% aqueous solution of sodium hydroxide, at 0° C. Extraction with ether, followed by washing with water, drying and concentrating, yielded 23 g of raw product. The latter was distilled firstly on a Vigreux column to give 17 g of 3-hexylpyridine (B.p. 65°-67° C./ 13 Pa). The product was further purified by means of a second distillation on Vigreux column to give 99.95% pure 3-hexylpyridine (yield: 47%).

The other 3-alkylpyridines were prepared in similar fashion, using the appropriate alkyl bromide. The analytical data of these synthetic compounds were the following:

3-hexylpyridine

Retention time (on apolar column SPB-1): 22.29 min.
NMR($^1$H, 360 MHz): 0.88(t, 3H); 1.2-1.4(m, 6H); 1.54-1.66(m, 2H); 2.59(t, 2H); 7.19(d×d, 1H); 7.49(d, 1H); 8.44(superimposed on 8.43, 2H) δ ppm.
MS: 163(M+, 10), 162(10), 148(3), 134(9), 120(33), 107(14), 106(85), 93(100), 92(70).
Detection treshold 0.28 ppb.

3-heptylpyridine

Retention time (on apolar column SPB-1): 25.39 min.
B.p.: 72°-74° C./13 Pa.
NMR($^1$H, 360 MHz): 0.88(t, 3H); 1.2-1.4(m, 8H); 1.54-1.66(m, 2H); 2.59(t, 2H); 7.19(d×d, 1H); 7.49(d, 1H); 8.44(superimposed on 8.43, 2H) δ ppm.
MS: 177(M+, 4),162(2),148(6),134(13),120(15),107(15), 106(75), 93(100), 92(40).

3-octylpyridine

Retention time (on apolar column SPB-1) 28.38 min.
B.p.: 108° C./13 Pa.
NMR($^1$H, 360 MHz): 0.88(t, 3H); 1.2-1.4(m, 10H); 1.54-1.66(m, 2H); 2.59(t, 2H); 7.19(d×d, 1H); 7.49(d, 1H); 8.44(superimposed on 8.43, 2H) δ ppm.
MS: 191(M+, 11), 162(8), 148(14), 134(7), 120(18), 107(19), 106(98), 93(100), 92(40).

5-Hexyl-2-methylpyridine was prepared starting from n-octanal according to the following method.

100 G (0.78 mmol) of n-octanal, 73 g of 36% formic aldehyde and 260 g (0.78 mol) of catalyst (aqueous diethylamine chlorhydrate; 3 mol/kg) were charged in a 3-neck flask. The mixture was heated to reflux for 1 h and distilled. The reaction product was extracted with ether, dried and concentrated to give 42.41 g of 2-hexyl-2-propenal. Extraction of the flask's residue provided yet 64 g of raw product. The aldehyde was used as such in the next step.

To a zinc iodide suspension (0.21 g, 0.671 mmol) in 42 g (0.3 mol) of 2-hexyl-2-propenal there were added dropwise, at 60° C. and under nitrogen, 18.5 g (0.25 mol) of 2-methoxypropene. Once the introduction was completed (23 min), the reaction was allowed to continue for 6 h at 60° C. and the mixture was then distilled on a Vigreux column to give 8.16 g of 5-hexyl-3,4-dihydro-2-methoxy-2-methyl-2H-pyran (B.p. 73°-74°/3 Pa; yield 15.4%).

This product was used in the following reaction.

To a solution containing 2.76 g (39.47 mmol) of hydroxylamine hydrochloride, 8.58 g (143.10 mmol) of acetic acid and 692 mg (38.49 mmol) of water, there were added dropwise, at 100° C. and under N$_2$, over 3 h, 8.16 g (38.49 mmol) of the hydroxypyran obtained in the preceding reaction. The reaction mixture was stirred for another 30 min at 100° C., cooled and poured over a mixture of NaOH and iced water. The aqueous solution was extracted 3times with ether and the ether solution washed 4times with 10% HCl and then once with water (salt). The aqueous solution was rendered alkaline at 0° C. with 20% NaOH. After another extraction with ether (twice), washing with water, drying, concentration and bulb-to-bulb distillation (130°-50° C./3 Pa), there were obtained 4.187 g (yield 62.2%) of 5-hexyl-2-methylpyridine, whose analytical data were the following:

NMR($^1$H, 360 MHz): 0.88(t, 3H); 2.47(s, 3H); 2.56(t, 3H); 7.06(d, J=5 Hz, 1H); 7.37(d×d, J=5.2 Hz, 1H); 8.31(d, J=2 Hz, 1H) δ ppm.
NMR($^{13}$C): 14.0(q); 22.6(t); 23.9(q); 28.9(t); 31.2(t); 31.7(t); 32.7(t); 122.8(d); 134.8(s); 136.2(d); 149.2(d); 155.6(s) δ ppm.
MS: 177(M+, 10), 176(5), 162(2), 148(4), 134(15), 120(30), 107(35), 106(100), 93(3), 79(13),77(19).

3-(4-Methylhexyl)pyridine was prepared in a similar manner to that described above with regard to 3-hexylpyridine but using 3-methyl-1-pentylbromide [prepared by adding over 1 h, at −30° C. and under N$_2$, 22.5 g of PBr$_3$ (0.083 mol; 7.8 ml) to a mixture of 21.6 g (0.212 mol) of 3-methyl-1-pentanol, 3.95 g of anhydrous pyridine and 88.4 ml of anhydrous sulfuric ether; the mixture was allowed to react for 1 h at −30° C. and then for 1 night at room temperature; the reaction product was extracted and washed in the usual manner and purified on a Vigreux column to provide 20.8 g of pure product].

300 Ml of liquid ammoniac, 4.62 g (0.201 mol) of Na, 7.1 g (76 mmol) of 3-methylpyridine and 14 g (84 mmol) of 3-methyl-1-pentyl bromide were used.

The analytical data of 3-(4-methylhexyl)pyridine were the following:

NMR($^1$H, 360 MHz, CDCl$_3$): 0.85(t, J=7 Hz, superimposed on d, J=7 Hz, 6H); 1.05-1.21(m, 2H); 1.25-1.40(m, 3H); 1.5-1.7(m, 2H); 2.58(t, J=7 Hz×d, J=1 Hz, 2H); 7.20(d×d, 1H); 7.49(d, 1H); 8.44(d, 1H); 8.44(d) superimposed on 8.45(s) (2H for the group) δ ppm.
MS: 177(M+, 10), 176(8), 162(9), 148(30), 134(5), 120(30), 107(33), 106(71), 93(100), 92(88), 65(26), 57(25), 43(28), 41(24), 39(15).

This pyridine developed a fatty, green, juicy and nutty flavor.

The invention will now be described in more detail by way of the examples presented hereinafter.

EXAMPLE 1

Application in orange essential oil

Five samples of orange essential oil were prepared with the following ingredients:

| Ingredient | Sample A | B | C | D | E |
|---|---|---|---|---|---|
| | % by weight | | | | |
| Florida orange essential oil | 100.0000 | 99.9975 | 99.9950 | 99.9950 | 99.9800 |
| 3-hexyl-pyridine | — | 0.0025 | — | — | — |
| 3-heptyl-pyridine | — | — | 0.0050 | — | — |
| 3-octyl-pyridine | — | — | — | 0.0050 | — |
| 5-hexyl-2-methyl-pyridine | — | — | — | — | 0.0200 |
| Total | 100.0000 | 100.0000 | 100.0000 | 100.0000 | 100.0000 |

A panel of expert flavorists evaluated the five samples A, B, C, D and E in an acid solution (10% sugar, 0.1% citric acid) at 0.1% in spring water, solution to which 300 ppm of orange oil sample had been added.

According to these experts, sample A had a sweet, aldehydic taste, typical of orange peel. Sample B had a more juicy character and possessed more body than essential oil A. The flavor of this sample B was also brighter and had more impact, its character being also more aldehydic. Sample C was sweeter, with more juice and zest character than sample A. It possessed also more body and a slightly fatty character.

As for sample D, the expert flavorists found it zesty and juicy and fuller than sample A, as well as having more body. It possessed a clean aldehydic note and some mandarine character.

Sample E was judged more juicy, with a more pronounced zesty character than sample A. It possessed also a more rounded, fuller and pulpy taste, while being sweeter and less terpenic.

EXAMPLE 2

Aromatic composition of the savory type

An aromatic base composition of the savory, surimi type was prepared by admixing the following ingredients:

| Ingredients | Weight (g) |
|---|---|
| Surimi | 400 |
| Salt | 10 |
| Iced water | 136 |
| Sugar | 8 |
| Potato starch | 20 |
| MSG* | 2 |
| Shrimp extract | 4 |
| Yeast extract | 2 |
| Albumin powder | 20 |
| Total | 602 |

*monosodium glutamate

With this surimi base composition, three novel aromatic compositions A, B and C were prepared, by adding to the surimi base respectively 50 ppb of 3-hexylpyridine, 200 ppb of 3-heptylpyridine and 200 ppb of 3-octylpyridine. The base composition and the three novel compositions A, B and C thus flavored were cooked at 90° C. for 30 min, chilled and deep frozen.

A panel of expert flavorists evaluated the three compositions A, B and C after de-freezing and compared them with the base composition cooked in identical fashion. According to the experts, the surimi base composition had a quite bland and sweet fishy taste, while composition A was sweeter and cleaner than the surimi base. It also had an enhanced seafood note and it was fuller and had more impact.

Composition B had a more fishy character than the base composition. It was also more fatty, with more shrimp character and improved impact.

As for composition C, it was judged to be improved over the base composition, its flavor being more fishy and meaty than that of the latter. In addition it had enhanced crab notes and more body than the surimi base.

EXAMPLE 3

Application in a commercial orange juice

Four samples of orange juice were prepared from a base orange juice obtained by dilution to single strength of a commercially available frozen processed concentrate. 25 Ppb of 3-hexylpyridine were added to this orange juice to prepare composition A, 50 ppb of 3-heptylpyridine to prepare composition B, 50 ppb of 3-octylpyridine to prepare composition C and 500 ppb of 5-hexyl-2-methylpyridine to prepare composition D.

The four novel compositions A, B, C and D were evaluated by a panel of expert flavorists, who compared them with the base orange juice which possessed a sweet, cooked, typical processed note.

According to the experts, composition A possessed a more green and fresher character than the base orange juice. It also had a more juicy impact and it covered the cooked character of the base.

Composition B had a fuller flavor and was sweeter and more juicy than the base orange juice. It was also slightly fatty and green, as well as smoother than the base juice, whose cooked note had also been covered.

Composition C, on the other hand, was found to be sweet and fruity, with a more fruity, juicy and green character than the base orange juice. Finally, composition D was sweeter and more juicy than the base orange juice, with more body and a less cooked, fresher character.

EXAMPLE 4

Preparation of a perfuming composition

A base perfuming composition was prepared by admixture of the following ingredients:

| Ingredients | Weight (g) |
|---|---|
| Geraniol | 15.0 |
| Phenethylol | 5.0 |
| Linalol | 31.5 |
| HEDIONE ®[1] | 10.0 |
| Methyl anthranilate | 2.5 |
| Petitgrain essential oil | 10.0 |
| Geranyl acetate | 5.0 |
| α-Terpineol | 5.0 |
| Orange flower essential oil | 15.0 |
| Total | 99.0 |

[1] methyldihydrojasmonate; origin: Firmenich SA, Geneva, Switzerland.

To this base composition there were added 0.1% by weight of 7-heptylpyridine, relative to the weight of composition, to give a novel composition which developed a dry, bitter and refreshing note, partially reminiscent of the odor of the orange flower absolute.

EXAMPLE 5

Preparation of a perfuming composition

A base perfuming composition was prepared by admixture of the following ingredients:

| Ingredients | Weight (g) |
|---|---|
| Terpenyl acetate | 15.0 |
| Geraniol | 15.0 |
| Linalol | 10.0 |
| Phenethylol | 15.0 |
| Eugenol | 5.0 |
| L-Carvone | 5.0 |
| Anethol | 2.5 |
| 4-(1,1-dimethylethyl)-1-cyclohexyl acetate[1)] | 15.0 |
| Violet essential oil | 2.5 |
| LILIAL ®[2)] | 5.0 |
| 10%* cis-3-Hexenol | 1.5 |
| Total | 91.5 |

*in dipropyleneglycol
[1)]isomer mixture cis:trans; origin: Firmenich SA, Geneva, Switzerland.
[2)]3-(4-tert-butyl-1-phenyl)-2-methylpropanal; origin: L. Givaudan, Vernier, Switzerland.

To this base composition there were added 0.1% in weight, relative to the weight of composition, of 3-heptylpyridine to provide a novel composition which developed a fresher and more diffusive, less sweet note than that of the base composition. The compound of the invention produced a green, herbal and floral effect, thus enhancing the spicy, minthy and violet character of the composition.

The same type of effect, albeit slightly less pronounced, was observed when 3-hexylpyridine was added at 0.1% by weight to the base composition.

What we claim is:

1. A process to confer, improve, enhance or modify the citrus or marine type organoleptic properties of a perfuming or flavoring composition, or of a perfumed or flavored article, which process comprises adding to said composition or article a compound of formula

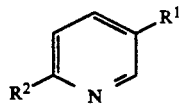

(I)

wherein $R^1$ stands for a saturated linear alkyl radical having 6 to 8 carbon atoms, or for a 4-methylhexyl radical, and $R^2$ represents either a hydrogen atom or, when $R^1$ has 6 carbon atoms, a hydrogen atom or a methyl radical.

2. A perfuming composition or a perfumed article having a citrus type odor containing as active ingredient a compound of formula I as defined in claim 1.

3. A perfuming composition or a perfumed article according to claim 2, wherein the active ingredient is 3-hexylpyridine or 3-heptylpyridine.

4. A perfumed article according to claim 2, in the form of a perfume or cologne, a soap, a bath or shower gel, a shampoo or any other hair-care product, a cosmetic preparation, a body or air deodorant, a detergent or fabric softener, or a household product.

5. A process to confer, improve, enhance or modify the citrus flavor character of a flavoring composition or a flavored article, which process comprises adding to said composition or article a compound of formula (I) as defined in claim 1.

6. A process according to claim 5, wherein the compound of formula (I) is added at a concentration of between about 20 ppb and 5 ppm of the total weight of said composition or article.

7. A citrus flavor character flavoring composition or flavored article containing as flavoring ingredient compound of formula (I) as defined in claim 1 essentially in its pure form.

8. A flavoring composition or flavored article according to claim 7, wherein the compound of formula (I) is present at a concentration of between about 20 ppb and 5 ppm of the total weight of said composition or article.

9. A process to improve the orange type flavor character in an article selected from the group consisting of a foodstuff, a beverage, a chewing gum, a toothpaste or a pharmaceutical preparation, which process comprises adding to said article a compound of formula (I) as defined in claim 1, at a concentration of between about 20 ppb and 5 ppm of the total weight of the article.

10. A process according to claim 1 wherein $R_1$ of formula (I) is 4-methylhexyl and $R_2$ is hydrogen.

11. A process according to claim 1 wherein the compound of formula (I) is present at a concentration of between about 20 ppb and 5 ppm of the total weight of said composition or article.

12. A perfuming composition or a perfumed article according to claim 2 wherein $R_1$ of formula (I) is 4-methylhexyl and $R_2$ is hydrogen.

13. A perfumed article according to claim 3 in the form of a perfume or cologne, a soap, a bath or shower gel, a shampoo or any other hair care product, a cosmetic preparation, a body or air deodorant, a detergent or fabric softener, or a household product.

14. A flavoring composition or flavored article according to claim 1 wherein $R_1$ of formula (I) is 4-methylhexyl and $R_2$ is hydrogen.

15. A process according to claim 7 wherein the compound of formula (I) is present at a concentration of between about 20 ppb and 5 ppm of the total weight of said composition or article.

16. A flavoring composition or flavored article according to claim 7 wherein $R_1$ of formula (I) is 4-methylhexyl and $R_2$ is hydrogen.

17. A process according to claim 9 wherein $R_1$ of formula (I) is 4-methylhexyl and $R_2$ is hydrogen.

* * * * *